United States Patent [19]
Klenk

[11] Patent Number: 4,490,307
[45] Date of Patent: Dec. 25, 1984

[54] PROCESS FOR THE PRODUCTION OF β-MERCAPTOPROPIONIC ACID DERIVATIVES

[75] Inventor: Herbert Klenk, Hanau, Fed. Rep. of Germany

[73] Assignee: Degussa Aktiengesellschaft, Frankfurt, Fed. Rep. of Germany

[21] Appl. No.: 504,422

[22] Filed: Jun. 15, 1983

[30] Foreign Application Priority Data

Jun. 26, 1982 [DE] Fed. Rep. of Germany ....... 3223973

[51] Int. Cl.$^3$ ................. C07C 121/16; C07C 149/20; C07C 149/237
[52] U.S. Cl. ................. 260/465.1; 560/147; 562/512
[58] Field of Search ........... 560/147; 562/512; 260/465.1

[56] References Cited

U.S. PATENT DOCUMENTS

| 2,268,185 | 12/1941 | Burke et al. | 562/147 |
| 2,748,172 | 5/1956 | Wordie | 260/465.1 |
| 3,502,708 | 3/1970 | Thoma et al. | 260/465.1 |
| 3,517,058 | 6/1970 | Thoma et al. | 562/512 |
| 3,551,499 | 12/1970 | Krockow | 562/512 |
| 3,840,586 | 10/1974 | Chiba et al. | 560/147 |

FOREIGN PATENT DOCUMENTS

| 1237563 | 3/1967 | Fed. Rep. of Germany . |
| 1238462 | 4/1967 | Fed. Rep. of Germany . |
| 2034172 | 1/1971 | Fed. Rep. of Germany . |
| 2244234 | 2/1974 | Fed. Rep. of Germany . |
| 1358019 | 6/1974 | United Kingdom ................ 560/147 |

OTHER PUBLICATIONS

E. Reid Organic Chemistry of Bivalent Sulfur, vol. I, p. 431, (1958).

Primary Examiner—Joseph P. Brust
Attorney, Agent, or Firm—Cushman, Darby & Cushman

[57] ABSTRACT

There is provided a process for the production of β-mercaptopropionic acid and its esters and nitriles by reacting the corresponding acrylic acid derivatives with trithiocarbonates in aqueous solution.

22 Claims, No Drawings

PROCESS FOR THE PRODUCTION OF β-MERCAPTOPROPIONIC ACID DERIVATIVES

BACKGROUND OF THE INVENTION

The invention is directed to a new process for the production of β-mercaptopropionic acid derivatives of the general formula (I):

$$H-S-CH_2-CH_2-X \qquad (I)$$

where X is —CN, —COOH or preferably —COOR, where R is alkyl.

It is known to produce β-mercaptopropionic acid derivatives by reacting β-chloropropionic acid derivatives with alkali hydrogen sulfide or with thiourea. These syntheses, however, are not satisfactory industrially because they take a long time or only give poor yields (E. Reid, Organic Chemistry of Bivalent Sulfur, Volume I, page 451).

Furthermore, it is known to react acrylonitrile with hydrogen sulfide to form β-mercaptopropionitrile. Hereby however, there must be used a considerable excess of hydrogen sulfide if yields of about 38% are to be produced. Besides it is necessary to carry out this reaction under pressure (Wordie U.S. Pat. No. 2,748,155).

Even in carrying out this process in the presence of a catalyst system consisting of a base and sulfur there cannot be eliminated the basic disadvantages of this process (German No. OS 2,034,172).

Finally it is known that a direct addition of hydrogen sulfide to an acrylic ester for the purpose of forming the mercaptopropionic acid ester is not possible since instead there is always obtained the thiodipropionate (Riddel, Monomeric Acrylic Esters, 1954, page 148). In order to avoid such a double addition it is known to react acrylic acid esters with alkali hydrogen sulfide using carbon disulfide as the reaction medium. In this reaction, however, there must also be used an organic solvent, for example, an alcohol. Thereby reference is made to the fact that to the greatest extent possible no water should be present in the reaction mixture, since otherwise there are preferably formed thiodipropionic acid esters. However, on an industrial scale it is very difficult to realize these water free conditions. Besides the working up is made difficult through the additional solvent, since as a rule it hinders the isolation of the mercapto derivatives from the acidified, aqueous reaction mixture and besides makes necessary a distillative separation of solvent and carbon disulfide (German Pat. No. 2,244,234).

SUMMARY OF THE INVENTION

It has now been found that β-mercaptopropionic acid derivatives of the general formula (I)

$$H-S-CH_2-CH_2-X \qquad (I),$$

in which X is —CN, —COOH, or preferably —COOR where R is an alkyl group have 1 to 18 carbon atoms, especially have 1 to 8 carbon atoms, preferably methyl, can be produced in high yields if an acrylic acid derivative of the general formula (II)

$$CH_2=CH-X \qquad (II),$$

where X is as defined above is reacted with an alkaline earth metal, alkali metal, or ammonium salt of trithiocarbonic acid in a mixture with water and an organic solvent, or preferably water alone, and the reaction mixture obtained, after acidification is worked up with a protonic acid is known manner.

The alkali or alkaline earth metal salt of trithiocarbonic acid needed for the reaction can be obtained in simple manner from carbon disulfide and the corresponding sulfide in aqueous solution. These trithiocarbonates for example correspond to the following formulae:

$$Na_2CS_3, K_2CS_3, CaCS_3, (NH_4)_2CS_3.$$

A particular advantage of the process of the invention is that the reaction can be carried out in water. However, it is also possible to use mixtures of water with water soluble or water insoluble organic solvents. Examples of such solvents are alcohols such as alkanols, e.g. methanol, ethanol, isopropanol and butanol and alkanediols, e.g. ethylene glycol. However, there can also be used for example acetone, dioxane, benzene, or methylene chloride.

The reaction of the invention proceeds very quickly. Therefore it is not necessary to use very high temperatures or elevated pressures. The presence of salt containing aqueous solutions also permits working below 0° C. Generally reaction temperatures can be kept between −25° C. and +80° C. Preferably the reactions are carried out in the temperature range between −10° C. and 40° C. The reaction can be carried out continuously or discontinuously.

The reaction can be carried out while maintaining a mole ratio of acrylic acid derivative (II) to salt of trithiocarbonic acid of 1:2. A smaller ratio is also possible, but has no further advantage. Generally there is maintained a ratio of from 1:1 to 1.5, preferably from 1:1 to 1.2. There can also be employed excess amounts of trithiocarbonate salts but generally, however, this results in no advantage.

During the reaction of trithiocarbonate with the acrylic acid derivative as a rule no free carbon disulfide reaction mixture is detectable. To set free the mercaptopropionic acid derivatives and the carbon disulfide according to the process of the invention in all there are needed at least 2 equivalents of acid per mole of trithiocarbonate employed. Also less than 2 equivalents can be used but as a rule this brings about no advantage.

The addition of these 2 equivalents of acid can take place after the end of the reaction. Considering the alkali sensitivity of specific acrylic acid esters, however, it can be advisable to add an amount of acid equivalent to the acrylate ester simultaneously with the reaction of the two components. As acids there can be employed any protonic acid. Especially suitable, however, are aqueous acids, such as phosphoric acid sulfuric acid, or especially hydrochloric acid.

The working up of the reaction mixture is carried out in known manner. For example the two phase mixture is separated and the organic phase fractionally distilled. Hereby the carbon disulfide can be isolated and in a given case be used again for the formation of the trithiocarbonate.

The β-mercaptopropionic acid derivatives producible according to the invention are valuable intermediate products for the production of pesticides and for the production of lacquer stabilizers. However, they can also be used as cosmetic products in the production of cold and permanent waving preparations.

Unless otherwise indicated all parts and percentages are by weight.

The process can comprise, consist essentially of, or consist of the stated steps with the recited materials.

EXAMPLE 1

There were present in a stirring apparatus 376 grams of a 45% aqueous sodium trithiocarbonate solution (corresponding to 1.1 mole). Under stirring at 1° C. there were simultaneously dropped in 86 grams of acrylic acid methyl ester (1.0-mole) and 100 ml of a 32% aqueous hydrochloric acid (1.0 mole). After the dropping in post stirring was continued for 10 minutes and then under further stirring there were added 150 ml of 32% hydrochloric acid. The two phase mixture formed was conveyed into a separatory funnel, the organic phase separated off and fractionally distilled. There were isolated 110.4 grams of β-mercaptopropionic acid methyl ester having a boiling point of 60° C. at 18 mbar. This corresponds to a yield of 92% based on the acrylic acid ester employed.

Besides there were recovered 76 grams of carbon disulfide.

EXAMPLE 2

The procedure was as described in Example 1 except in place of methyl acrylate there were employed 128 grams (1.0 mole) of butyl acrylate and the reaction was carried out at +20° C. There were isolated 136 grams (corresponding to a yield of 84%) of β-mercaptopropionic acid butyl ester having a boiling point of 102° C. at 18 mbar by the use of fractional distillation. Additionally, there was obtained 75 grams of carbon disulfide.

EXAMPLE 3

The procedure was as described in Example 1 but instead of methyl acrylate there were employed 53 grams (1.0 mole) of acrylonitrile. After the acidification with hydrochloric acid and the phase separation the aqueous phase was shaken once with ether. The combined phases ($CS_2$ and ether phase) were then fractionally distilled. There were obtained 62 grams of β-mercaptopropionitrile having a boiling point of 82° C. at 20 mbar. This corresponds to a yield of 71% based on the acrylonitrile employed.

EXAMPLE 4

The procedure was as described in Example 1 but in place of methyl acrylate there were employed 184 grams of octyl acrylate and first there were added 250 ml of dilute $H_2SO_4$ (4N) and the later 300 ml of dilute $H_2SO_4$. After the fractional distillation there were isolated 174.5 grams (corresponding to a yield of 80%) of 3-mercaptopropionic acid octyl ester.

EXAMPLE 5

The procedure was as described in Example 1 but in place of methyl acrylate there were employed 352 grams of 92% octadecyl acrylate (1.0 mole). After the acidification the entire reaction mixture was filtered, whereby there remained behind 350 grams of a white solid which, after the drying at above 40° C. began to melt. Elemental analysis showed an —SH content of 8.3%.

EXAMPLE 6

There were present in a stirring apparatus 577.5 grams of a 40% sodium trithiocarbonate solution (corresponding to 1.5 moles). Under stirring at −10° C. there were dropped in 128 grams of isobutyl acrylate (1.0 mole). Post stirring was continued for a further 10 minutes and then the mixture was acidified with 350 ml of 32% hydrochloric acid. After the phase separation the organic phase was fractionally distilled. There were obtained 128 grams of mercaptopropionic acid isobutyl ester (corresponding to a yield of 79%).

EXAMPLE 7

The procedure was as described in Example 6 but in place of isobutyl acrylate there were employed 53 grams (1.0 mole) of acrylonitrile. After extraction of the reaction mixture with ether and subsequent fractional distillation there were obtained 63.5 grams (73% yield) of β-mercaptopropionitrile.

EXAMPLE 8

There were hourly separately fed via two pumps an amount of 627 grams of a 54.1% sodium trithiocarbonate solution (=2.2 mole/h) and 79.2 grams of acrylic acid (=1.1 moles/h) into a small reaction flask having a capacity of 40 ml which had an overflow and was stirred with a magnetic stirrer. By means of external cooling a temperature below 20° C. was maintained in the reactor. The solution flowing out of the reaction flask after some residence time passed into a second reaction flask having a capacity of 35 ml which likewise had an overflow as well as a deaeration unit and into which there were fed per hour 550 ml of 25% hydrochloric acid. The emulsion flowing out of the reactor was collected batchwise. The two phase mixture formed was separated, the aqueous phase extracted with ether and the collected organic extracts fractionally distilled. Thus from a batch which discharged from the second reaction flask in one hour there were obtained 70.4 grams of β-mercaptopropionic acid having a boiling point of 113°–117° C. at 18 mbar. This corresponded to a yield of 60.4% based on the acrylic acid. The β-mercaptopropionic acid solidified upon cooling below 16° C.

What is claimed is:

1. A process for the production of a β-mercaptopropionic acid derivative of formula (I)

H—S—CH$_2$—CH$_2$—X    (I), where X is —CN, —COOH, or —COOR where R is an alkyl group having 1 to 18 carbon atoms comprising reacting an acrylic acid derivative of the formula (II)

CH$_2$=CH—X    (II)

with an alkaline earth metal disalt of trithiocarbonic acid, alkali metal disalt of trithiocarbonic acid, or ammonium disalt of trithiocarbonic acid in a solvent which is water alone or a mixture of water and an organic solvent, acidifying the reaction mixture obtained with a protonic acid and recovering the β-mercaptopropionic acid derivative of formula (I).

2. A process according to claim 1 wherein there is prepared a compound of formula (I) where X is —CN.

3. A process according to claim 1 wherein there is prepared a compound of formula (I) where X is —COOH.

4. A process according to claim 1 wherein there is prepared a compound of formula (I) where X is —COOR.

5. A process according to claim 4 wherein R is an alkyl group of 1 to 8 carbon atoms.

6. A process according to claim 5 wherein the solvent is water alone.

7. A process according to claim 6 wherein the reaction temperature is between −10° C. and +40° C.

8. A process according to claim 7 wherein the mole ratio of acrylic acid derivative of formula (II) to the salt of trithiocarbonic acid is between 1:1 and 1:1.2.

9. A process according to claim 8 wherein there is added one equivalent of protonic acid per mole of salt of trithiocarbonic acid during the reaction and at least one equivalent of protonic acid per mole of salt of trithiocarbonic acid after the reaction.

10. A process according to claim 9 wherein the protonic acid is hydrochloric acid.

11. A process according to claim 1 wherein the protonic acid is phosphoric acid, sulfuric acid, or hydrochloric acid.

12. A process according to claim 1 wherein there are employed at least two equivalents of protonic acid per mole of salt of trithiocarbonic acid employed.

13. A process according to claim 1 wherein there is employed water alone.

14. A process according to claim 1 wherein there is employed a mixture of water and a lower alkanol, glycol, acetone, dioxane, benzene, or methylene chloride.

15. A process according to claim 1 wherein the reaction temperature is between −25° C. and +80° C.

16. A process according to claim 15 wherein the reaction temperature is between −10° C. and +40° C.

17. A process according to claim 15 wherein the mole ratio of acrylic acid derivative of formula (II) to the salt of trithiocarbonic acid is between 1:1 and 1:2.

18. A process according to claim 17 wherein the mole ratio of acrylic acid derivative of formula (II) to the salt of trithiocarbonic acid is between 1:1 and 1:1.2.

19. A process according to claim 1 wherein the mole ratio of acrylic acid derivative of formula (II) to the salt of trithiocarbonic acid is between 1:1 and 1:2.

20. A process according to claim 1 wherein there are employed at least two equivalents of protonic acid per mole of salt of trithiocarbonic acid employed.

21. A process according to claim 17 wherein there are employed at least two equivalents of protonic acid per mole of trithiocarbonic acid employed.

22. A process according to claim 21 wherein the salt of trithiocarbonic acid is $Na_2CS_3$, $K_2CS_3$, $CaCS_3$ or $(NH_4)_2CS_3$.

* * * * *